United States Patent [19]
Bates

[11] Patent Number: 6,165,129
[45] Date of Patent: Dec. 26, 2000

[54] REMOVABLY MOUNTABLE PULSE RATE MONITORING SYSTEM

[76] Inventor: Roger D. Bates, 6007 Spring Flower Trail, Dallas, Tex. 75248

[21] Appl. No.: 09/249,750

[22] Filed: Feb. 12, 1999

[51] Int. Cl.[7] ........................................................ A61B 5/02
[52] U.S. Cl. ............................ 600/481; 600/520; 600/382
[58] Field of Search ...................................... 600/481, 382, 600/509, 520, 521; 482/53, 62, 112

[56] References Cited

U.S. PATENT DOCUMENTS

| | | |
|---|---|---|
| 3,702,113 | 11/1972 | Blockley . |
| 4,319,581 | 3/1982 | Cutter . |
| 4,572,207 | 2/1986 | Yoshimi et al. . |
| 5,314,389 | 5/1994 | Dotan . |
| 5,337,753 | 8/1994 | Lekhtman . |
| 5,365,934 | 11/1994 | Leon et al. . |
| 5,738,104 | 4/1998 | Lo et al. .............................. 600/509 X |

OTHER PUBLICATIONS

Webster's II New Riverside Dictionary, The Riverside Publishing Company, 1994. see p. 267.

*Primary Examiner*—Max Hindenburg
*Assistant Examiner*—Ryan Carter
*Attorney, Agent, or Firm*—Haynes and Boone, LLP; Michael S. Bush

[57] ABSTRACT

A removably mountable pulse rate monitoring system and an associated exercise machine. The pulse rate monitoring system includes first, second and third housings, each configured for removable attachment to a support bar system of the exercise machine. Supportably mounted within the first housing is a pulse rate calculation circuit and a display, coupled to the pulse rate calculation circuit, for displaying a pulse rate determined by the pulse rate calculation circuit. A first electrode is supportably mounted by the second housing and a second electrode is supportably mounted by the third housing. The first and second electrodes transmits data used to determine the pulse rate of a user of the exercise machine when the electrodes are grasped by the user. Preferably, each of the second and third housings are configured as generally tubular sidewalls having an outer surface on which the electrode is mounted, an inner surface which defines an interior space, a first side surface which extends along the length of the first sidewall and a second side surface which extends along the length of the first sidewall. The housing is deformable to space the first and second side surfaces apart from each other to define an access aperture which extends along the length of the sidewall. The access aperture defined by the first and second side surfaces of the sidewall enable the housing to be place over the support structure at a desired location.

26 Claims, 3 Drawing Sheets

REMOVABLY MOUNTABLE PULSE RATE MONITORING SYSTEM

TECHNICAL FIELD

The invention relates generally to exercise machines and, more particularly, to a pulse rate monitoring system suitable for removable attachment onto a wide variety of exercise machines.

BACKGROUND OF THE INVENTION

A number of exercise machines such as treadmills and stationary bicycles are particularly well suited for cardiovascular conditioning. Accordingly, it is often desirable to equip such exercise machines with a device capable of monitoring the pulse rate of a user as he or she exercises and displaying the monitored pulse rate in "real-time." Such real-time displays of pulse rate provides the user with invaluable feedback as to the quality of the workout. For example, users often seek to maintain an elevated pulse rate for a predetermined time period and need a pulse rate monitor in order to determine that the target elevated pulse rate has been reached.

As a result, for a number of years, many exercise machines have been equipped with pulse rate monitors. To measure the pulse rate of a user of an exercise machine, a pulse rate monitor must include some type of sensor which comes into physical contact with the user. Certain early designs of pulse rate monitors included a sensor (or sensors) clipped onto the finger or ear. Other designs located the sensor on a strap which wrapped around the waist. An electrical cable would then extend from the sensor in contact with the body to the circuit which calculates pulse rate from the data collected by the sensor. However, as sensors which attached directly to the body were often viewed as being uncomfortable to wear and/or annoying to use, the incorporation of pulse rate monitoring systems into exercise machines remained limited.

The aforementioned deficiency has been overcome in recent years by physically incorporating the sensors into the support structure of the exercise machines. For example, U.S. Pat. No. 5,337,753 to Lechtman discloses a heart rate monitor in which the electrodes which must be placed in contact with the body are disposed on the outer surface of an elongate hollow cylindrical member while the circuitry which calculates the heart rate is housed within the member. Lechtman further discloses that the cylindrical member may be attached to the handlebar of a stationary bicycle where it may be readily gripped by the user. Similarly, some treadmills are designed such that electrodes are formed at selected locations along side bars of the exercise machine while pulse monitoring circuitry is incorporated into a control pad used to operate the machine. While such pulse rate monitoring systems have proven to be quite popular, there remain a number of deficiencies associated therewith. First, the electrodes are fixed in a position deemed by the manufacturer as the preferred position for grasping the treadmill while exercising. However, individual preferences often vary. For example, while the manufacturer may have located the electrodes at the general center of each side bar, some users may prefer to grasp the side bars much closer to the front of the machine while others prefer to grasp a front bar of the exercise machine with both hands. If the electrodes are located anywhere besides the precise location where a user prefers to grasp the exercise machine, the pulse monitoring system may be deemed to be an annoyance to use. This is a particular concern in private clubs, gyms and other exercise facilities which strive to purchase machines which will appeal to the largest possible portion of its membership. Another problem is that such pulse monitoring systems can only be readily installed during the manufacture of the exercise machine. As exercise machines which incorporated such pulse rate monitoring systems did not appear in significant numbers until the last few years, many exercise machines purchased a number of years ago, but which are still in use, lack such pulse rate monitoring systems. Upgrading the exercise machines to a newer model which includes a pulse rate monitoring system is rarely an option, particularly in the home market where the relatively high cost (often exceeding $2,000) of high quality exercise machines presents a considerable bar to the replacement of the machine simply because it lacks a pulse rate monitor.

There are a number of pulse rate monitoring systems suitable for use as "after-market" retrofits. For example, U.S. Pat. No. 4,319,581 to Cutter discloses a heart pulse monitoring apparatus which may be slid over the handlebars of an stationary bicycle. However, the device disclosed in Cutter is not suitable for use in conjunction with many exercise machines such as those characterized by side bars for which the ends thereof are integrally formed with or otherwise attached to the remainder of the frame of the exercise machine. Recently, an after-market pulse rate monitoring system suitable for use with certain models of the Trimline treadmills manufactured by Hebb Industries, Inc. of Tyler, Tex. was introduced. The pulse rate monitoring system is comprised of an elongated, generally cylindrical bar which extends about two feet in length. Formed roughly two-thirds of the way between the general center and the respective ends are the bar are first and second electrodes designed to be grasped by a user. Each of the electrodes are electrically connected to a pulse rate detection and display device snap-mounted onto the bar at the general center thereof by conductors which extend along an interior passageway of the bar. When the pulse rate monitoring system is turned on and the operator grasps each of the electrodes with a respective hand, the user's pulse rate will appear on the display located at the general center of the bar.

Fixedly attached to the respective ends of the bar are mounting clamps sized to receive a generally tubular side bar of a Trimline treadmill. To mount the pulse rate monitoring system to a Trimline treadmill, a removable portion of each clamp is detached. The clamps are placed over the side bar and the removable portion resecured to the remainder of the clamp to mount the pulse rate monitoring system to the treadmill. On one side, the removable portion snappingly engages the clamp and, on the other, the removable portion is screw-mounted to the clamp. While this pulse rate monitoring system is suitable for mounting to an existing treadmill having side bars ill-suited for slidingly receiving a pulse rate monitoring system onto the ends thereof, the foregoing pulse rate monitoring system is equally limited in its range of applications. Specifically, the bar has a specified length and the clamps are fixed in location to the remainder of the bar. As a result, the pulse rate monitoring system may only be mounted onto treadmills or other exercise machines which have a pair of side bars separated by approximately 27 inches. However, side bars for treadmills are often separated by as much as 34 inches. For such treadmills, the bar could not be mounted to the machine. Indeed, the pulse monitoring system cannot be used with many of the exercise machines manufactured by Trimline itself. Thus, the pulse monitoring system is not particularly well-suited to be moved between machines. Finally, like all other pulse rate monitoring systems, the Trimline system requires that the user grasp the electrodes at set locations which may or may not be the locations where the user is most comfortable with.

Therefore, what is needed is a removably mountable pulse rate monitoring system suitable for use with a wide variety of exercise machines and which allows the electrodes thereof to be placed at a location preferred by the user and not mandated by the design of the device. It is, therefore, the object of this invention to provide such a device.

SUMMARY OF THE INVENTION

In one embodiment, the present invention is of a removably mountable pulse rate monitoring system which includes a tubular member having at least one electrode disposed on its outer side surface and a pulse rate monitor electrically connected to the at least one electrode. The tubular member is openable along its length to provide access to an interior space defined by an inner side surface thereof. Preferably, access is provided by an access opening defined by first and second side surfaces of the tubular member and which longitudinally extends along the length of the tubular member.

In one aspect thereof, the first interior side surface is movable, relative to the second interior side surface, between a first position in which the first and second interior side surfaces engage each other and the access opening is closed and a second position in which the first and second interior side surfaces are spaced apart from each other and the access opening is open.

In another aspect thereof, the tubular member is comprised of first and second parts, each having an outwardly curved top surface, an inwardly curved bottom surface and first and second side surfaces. The first side surface of the first part is pivotably mounted to the first side surface of the second part to enable the first part to pivot between first and second positions. In the first position, the second side surfaces of the respective parts engage each other and the first and second parts collectively form an open ended tube having a first length and an interior area defined by the bottom surfaces of the first and second parts. In the second position, the second side surface of the first part is spaced apart from the second side surface of the second part to define an access opening through which a bar having a second length greater than the first length may be inserted.

In still further aspects thereof, each of the first and second parts may include one or more hinge tabs which are attached to corresponding hinge tabs of the other part to pivotably mount the first and second parts together. A spring mounted between first and second ones of the hinge tabs biases the second side surface of the first part into engagement with the second side of the first part. Finally, the at least one electrode disposed on the tubular member may be configured to include a first electrode mounted on the top surface of the first part and a second electrode mounted on the top surface of the second part.

In further embodiments, the present invention is of an exercise machine and an associated pulse rate monitoring system to be used in conjunction with the exercise machine. The pulse rate monitoring system includes first, second and third housings, each configured for removable attachment to a support bar system of the exercise machine. Supportably mounted within the first housing is a pulse rate calculation circuit and a display, coupled to the pulse rate calculation circuit, for displaying a pulse rate determined by the pulse rate calculation circuit. A first electrode is supportably mounted by the second housing and a second electrode is supportably mounted by the third housing. The first and second electrodes transmits data used to determine the pulse rate of a user of the exercise machine when the electrodes are grasped by the user.

In one aspect, each of the second and third housings are configured as generally tubular sidewalls having an outer surface on which the electrode is mounted, an inner surface which defines an interior space, a first side surface which extends along the length of the first sidewall and a second side surface which extends along the length of the first sidewall. The housing is deformable to space the first and second side surfaces apart from each other to define an access aperture which extends along the length of the sidewall. The access aperture defined by the first and second side surfaces of the sidewall enable the housing to be place over the support structure at a desired location.

In another aspect, the tubular sidewalls are comprised of first and second parts, each having an outwardly curved top surface, an inwardly curved bottom surface and first and second side surfaces. The first side surfaces are pivotably mounted to each other so that the first part may be pivoted, relative to the second part, between first and second positions. In the first position, the second side surfaces of the first and second parts engage each other and, in the second position, the second side surface of the first and second parts define an access aperture through which a support bar having a length greater than the length of the housing may be inserted.

In still another aspect, each one of the first and second parts further include at least one hinge tab attached to a corresponding hinge tab of the other part to pivotably mount the first and second parts to each other. A biasing spring mounted between the hinge tabs biases the second side surfaces of the parts so that the access aperture is normally closed.

In still yet another aspect, the first housing has a first exterior side surface, a second exterior side surface, an interior side surface which defines an interior space in which the pulse rate calculation circuit is positioned and an interior passageway extending between the exterior side surfaces and through the interior space. Electrical cables are coupled to respective ones of the electrodes on one end and to the pulse rate calculation circuit on the other. These cables access the pulse rate calculation circuit through the passageway. In another aspect, the first housing is clamped over the support bar such that the support bar extends through the passageway.

In still another embodiment, the present invention is of a method for installing a pulse rate monitoring system in an exercise machine. A first electrode is clamped onto a first length of a support bar system of the exercise machine. A second electrode is then clamped onto a second length of the support bar system. A pulse rate monitor electrically connected to the electrodes is then attached onto the exercise machine. In use, the pulse rate monitor determines a pulse rate from data received from the electrodes. In alternate aspects of this embodiment of the invention, the first and second electrode may be respectively clamped onto first and second side bars of the support bar system or may be both clamped onto the front bar. In another aspect, the electrode is first mounted onto an exterior side surface of a generally tubular insulative housing. The tubular housing is then attached to the support bar system such that the first length of the support bar system is received within a generally cylindrical interior passageway formed within the tubular housing. Preferably, to attach the housing to the support bar system, the first length of support bar system is inserted through an access aperture which extends along the length of the tubular housing.

BRIEF DESCRIPTION OF THE DRAWINGS

The invention will be better understood and its numerous objects and advantages will become apparent to those skilled in the art by reference to the following drawings in which.

DETAILED DESCRIPTION

Figure 1:
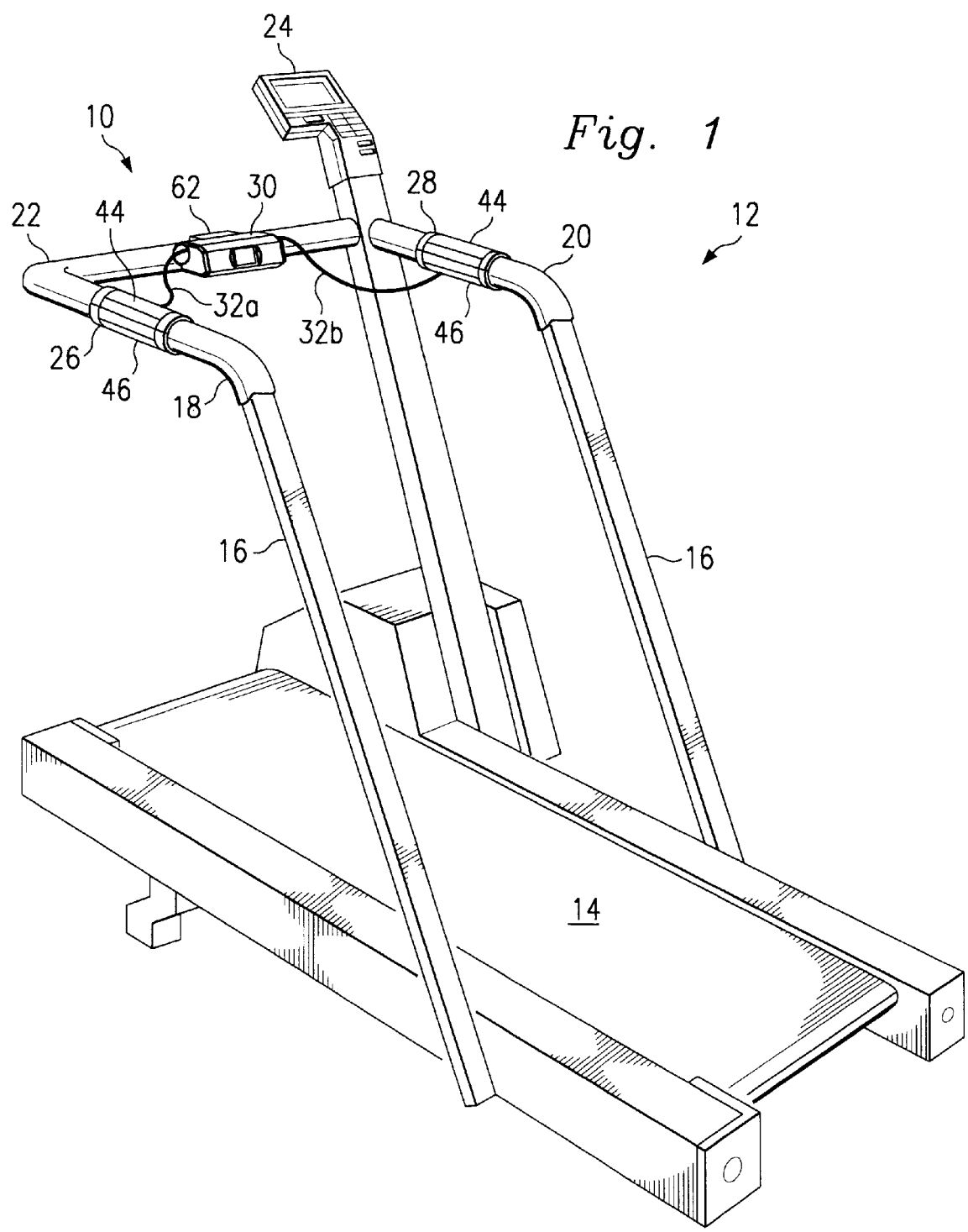
FIG. 1 is a perspective view of a removably mountable pulse rate monitoring system constructed in accordance with the teachings of the present invention and mounted to a conventionally designed treadmill.

Referring first to FIG. 1, a removably mountable pulse rate monitoring system 10 constructed in accordance with the teachings of the present invention will now be described in greater detail. As shown in FIG. 1, the pulse rate monitoring system 10 is mounted onto a treadmill 12. It is fully contemplated, however, that the pulse rate monitoring system 10 is equally suitable for mounting onto a wide variety of exercise machines besides those specifically illustrated herein.

The treadmill 12 includes a platform 14 on which a user initially stands (and later walks and/or runs) while exercising. Coupled to the platform 14 is a support frame 16 which partially surrounds the platform 14. Oftentimes, the support frame 16 is grasped by the user to enhance their balance while using the treadmill 12. As illustrated herein, the support frame 16 includes a first side bar 18, a second side bar 20 and a front bar 22. Each of the side and front bars 18, 20 and 22 have a generally cylindrical shape and a generally horizontal orientation parallel to the platform 14. Finally, the treadmill 12 further includes a display 24 typically used by the exercise to control operation of the treadmill 12. Of course, the support frame 16 shown in FIG. 1 is purely exemplary and that support frames are arranged in a wide variety of configurations which may include bars of different shapes, sizes and/or orientations. Furthermore, the term "platform" encompasses both the physical structure on which the user stands or sits as well as the exercise mechanism operated by the user during an exercise routine. When using the treadmill 12 or other exercise machine, a user will oftentimes grasp or otherwise touch one or more of the bars 18, 20 and 22, typically, to enhance their sense of balance while walking or running on the platform 14. Generally, the particular ones of the bars 18, 20 and 22 which are grasped, as well as the locations where they are grasped, are a matter of personal preference which tends to vary from user to user. For example, some users prefer to grasp the first side bar 18 with one hand and the second side bar 20 with the other. Others prefer to grasp the front bar 22 with both hands.

Figure 2:
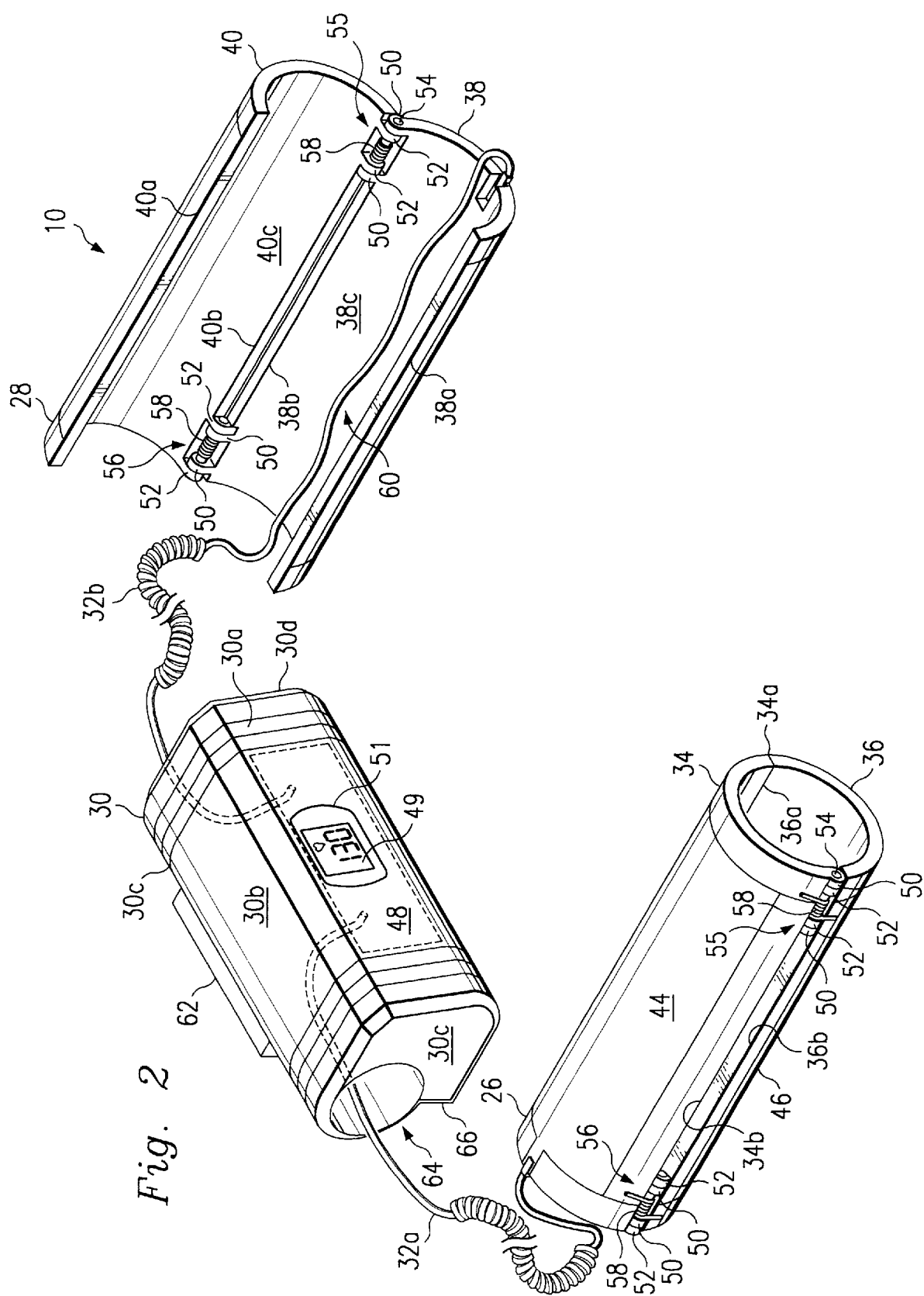
FIG. 2 is a front view of the removably mountable pulse rate monitoring system of FIG. 1.

Referring next to FIGS. 1 and 2, the removably mountable pulse rate monitoring system 10 will now be described in greater detail. As may now be seen, the removably mountable pulse rate monitoring system 10 includes first, second and third members 26, 28 and 30, each of which is mounted onto the support frame 16 at respective locations, electrically connected to each other by cables 32a and 32b.

As will be more fully described below, the first and second members 26 and 28 house electrodes for the pulse rate monitoring system 10. The remainder of the pulse rate monitoring system 10 is housed in the third member 30. More specifically, supportably mounted within an interior area of the third member 30 is a pulse rate calculation circuit 48 which receives data transmitted from electrodes in physical contact with the user and determines, from the received data, a pulse rate for the user. The pulse rate calculation circuit 48 is comprised of plural electronic components mounted on a printed circuit board. Coupled to the pulse rate calculation circuit 48 is a display 49, for example, an LCD display. While supportably mounted within the third member 30, the display 49 is visible to the user through an aperture 51 formed in a front side surface 30a of the third member 30.

As illustrated in FIG. 1, the third member 30 is mounted to the front bar 22 of the support frame 16. However, it is fully contemplated that the third member 30 may be mounted to any desired location along the support frame 16 or any other suitable location along the treadmill 12. It is further contemplated that the third member 30 may be mounted to the front bar 22 or other suitable location using a variety of techniques. For example, as illustrated in FIG. 1, a flap 62 of material, for example, nylon, may be fixedly attached to a top side surface 30b of the third member 30. The flap may then be wrapped tightly around the front bar 22 and then removably affixed to the front side surface 30a of the third member 30, for example, using respective strips of a hook and pile material such as velcro. Alternately, the third member 30 may be mounted to the front bar 22 using respective strips of the hook and pile material on the front bar 22 and on a back side surface 30c of the third member 30. It is further contemplated that the third member 30 may be mounted to the front bar 22 by inserting the front bar 22 into the interior passageway 64 which extends between first and second side surfaces 30c and 30d. Of course to mount the third member 30 to the front bar 22 in this manner, it would be preferable to enlarge the size of the interior passageway 64. In one configuration, the front bar 22 may be inserted into the passageway 64 by removing all or part of the rear side wall 66 of the third member 30 to expose the passageway 64, inserting the front bar 22 into the passageway 64 and then reattaching the rear side wall 66. Alternately, the rear side wall 66 could be screw or snap-mounted onto the remainder of the third member 30. In another configuration, as more fully described below, the third member 30 could be configured to be openable in a manner similar to the first and second members 26 and 28.

Continuing to refer to FIGS. 1 and 2, each of the first and second members 26 and 28 are generally cylindrically-shaped tubes formed of a non-conductive material such as a hardened plastic material. The first tubular member 26 is comprised of first and second parts 34 and 36, each having a general "C"-shaped cross-section, pivotably mounted to one another along one side. Thus, each of the tubular members 26 and 28 may be pivoted between a closed position (see first tubular member 26 in FIG. 2) in which a first interior side surface 34a of the first C-shaped part 34 engages a first interior side surface 36a of the second C-shaped part 36 and an open position (see second tubular member 28 in FIG. 2) in which the first interior side surfaces 38a and 40a have been separated by grasping each of the first and second C-shaped parts 38 and 40 in separate hands and pulling the two apart. In this manner, each of the first and second members 26 and 28 are openable along their length.

The first and second C-shaped parts 34 and 36 are pivotably mounted to each other along second interior side surfaces 34b and 36b while the first and second C-shaped parts 38 and 40 are pivotably mounted to each other along second interior side surfaces 38b and 40b. More specifically, projecting from the second interior side surfaces 34b and 38b of the first C-shaped parts 34 and 38 are a first series of hinge tabs 50. Similarly, projecting from the second interior side surfaces 36b and 40b are a second series of hinge tabs 52. Each hinge tab 50 is pivotably coupled to a corresponding hinge tab 52, for example, using a hinge pin 54. While any number of hinge tabs 50, 52 may be used to pivotably mount the first and second C-shaped parts 34 and 36, 38 and 40, as illustrated herein, the use of four hinge tabs 50, two formed along each of the upper and lower ends of each of the first C-shaped parts 34 and 38, are mated with four corresponding hinge tabs 52, two formed along each of the upper and lower ends of each of the second C-shaped parts 36 and 40 to form first and second hinges 55 and 56 has proven suitable for use.

Mounted within each hinge 55 and 56, specifically, between adjacent pairs of hinge tabs 50, 52, is a biasing spring 58 which exerts a spring force which biases the first and second C-shaped parts 34 and 36, 38 and 40 towards the closed position in which the first interior side surfaces 34a and 36a, 38a and 40a engage each other. Thusly, the first and second tubular members 26 and 28 are normally in the closed position. To mount one of the tubular members, for example, the second tubular member 28, to a support bar, for example, the side bar 20, the user grasps one of the C-shaped parts 38 and 40 and pulls the other of the C-shaped parts 38 and 40 to separate the first interior side surfaces 38a and 40a. By separating the first interior side surfaces 38a and 40a from engagement with each other, an access aperture which provides access to an interior space 60 defined by inner side surfaces 38c and 40 of the C-shaped parts 38 and 40 and which is defined by the first interior side surfaces 38a and 40a is formed.

After separating the first and second interior side surfaces 38a and 40a, the second tubular member 28 is placed over the side bar 20 such that the side bar 20 passes through the access aperture and is received in the interior space 60. The C-shaped parts 38 and 40 are released, thereby permitting the biasing springs 58 to drive the first and second interior side surfaces 38a and 40a back into engagement with each other to clamp the second tubular member 28 onto the side bar 20. To enhance the frictional engagement between the side bar 22 and the inner side surfaces 38c and 40c of the second tubular member 28 when clamped onto the side bar 20, it is preferred that second tubular member 28 is sized such that the interior space 60 has a generally cylindrical shape similarly dimensioned to the generally cylindrical side bar 20. To remove the second tubular member 28 mounted on the side bar 20, the first and second C-shaped sections 38 and 40 are separated and the second tubular member 28 pulled off of the side bar 20.

From the foregoing description, the numerous advantages of the first and second tubular member 26 and 28 over prior devices should be readily appreciated by one skilled in the art. First, they enable a pulse rate monitoring system to be readily installed onto an exercise machine. For example, the treadmill 12 lacks a pulse rate monitoring system. However, by clamping the first and second tubular members 26 and 28 onto the first and second side arms 18 and 20, the ready installation of the pulse rate monitoring system 10 onto the treadmill 12 is permitted. Next, the first and second tubular members 26 and 28 may be mounted at any desired location along the support frame 16 of the treadmill 12. For example, in FIG. 1, the first and second tubular members 26 and 28 are mounted onto the first and second side bars 18 and 20, respectively. However, if a user prefers to grasp the front bar 22 while exercising, the first and second tubular members 26 and 28 may be quickly mounted onto the front bar 22. The first and second tubular members 26 and 28 are also easily mounted on portions of the support frame 16 which are not shaped to readily receive prior devices. For example, the side bars 18 and 20 are formed as a whole with the remainder of the support frame 16. As a result, prior devices which were mounted on exercise machines by sliding the devices onto bars of the support frame cannot be mounted on the support frame 16. Finally, the pulse rate monitoring system 12 may be readily moved between exercise machines.

Continuing to refer to FIGS. 1 and 2, disposed on each of the first and second tubular members 26 and 28 are a pair of electrodes 44, 46, each formed of a conductive material such as metal. As illustrated herein, the electrodes 44, 46 are inserted into recesses (not shown) formed in the first and second tubular members 26 and 28. Alternately, the electrodes 44 and 46 may simply be fixedly mounted to, for example, using a glue or other adhesive material, or otherwise formed on, an exterior side surface of the tubular members 26 and 28. Each electrode 44, 46 mounted on the first tubular member 26 is coupled to the electrical cable 32a. Similarly, each electrode 44, 46 mounted on the second tubular member 28 is coupled to the electrical cable 32b. As illustrated herein, a portion of the first and second tubular members 26 and 28 underlying the first and second electrodes 46 and 48 is cut-away and the electrical cables 32a and 32b are coupled to the electrodes 46 and 48 overlaying the cut-away portion of the first and second tubular members 26 and 28 using an alligator clip or other type of clamp. Of course, it may be preferable to establish a permanent electrical coupling between the electrical cables 32a and 32b and the electrodes 44 and 46 using any one of a variety of suitable techniques, for example, by soldering one end of each of the cables 32a and 32b to each of the first and second electrodes 44 and 46. The other ends of the cables 32a and 32b are inserted into the interior passageway 64 and electrically connected to the pulse rate calculation circuit 48, for example, by soldering the ends of the cables 32a and 32b to the printed circuit board on which the pulse rate calculation circuit 48 resides.

The pulse rate monitoring system 10 is operated in the following manner. First, the pulse rate monitoring system 10 is powered up, for example, by a power supply (not shown) such as a battery. Power-up, which may occur either before or after the pulse rate monitoring system 12 is mounted to the treadmill 12, may be initiated by depressing an on/off switch (also not shown) or by simply connecting the battery to the power-demanding components residing on the pulse rate calculation circuit 48 and the display 49. Once the pulse rate monitoring system 10 is both mounted to the treadmill 12 and powered-up, the user begins an exercise routine using the treadmill 12. When the user decides to monitor his or her pulse rate, he or she physically contacts the electrodes 44 and 46, for example, by grasping the first and second tubular members 26 and 28. The electrodes 44 and 46 transmit data to the pulse rate calculation circuit 48 where the user's pulse rate is determined. The determined pulse rate then appears on the display 49.

Figure 3:
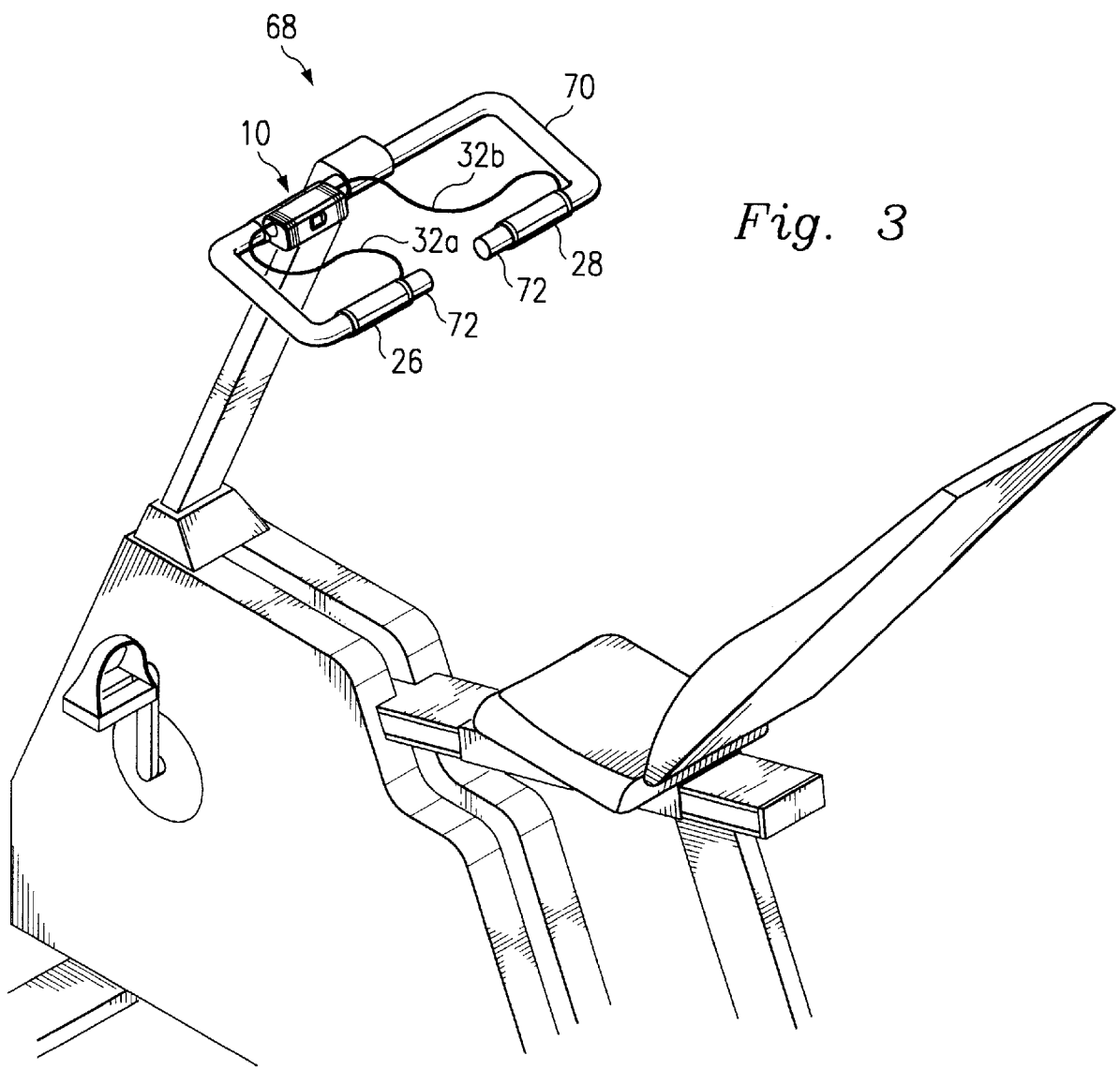
FIG. 3 is a perspective view of the removably mountable pulse rate monitoring system of FIGS. 1–2, now mounted to a conventionally designed stationary bicycle.

Referring next to FIGS. 1 and 3, the flexibility of the removably mountable pulse rate monitoring system 10 in use may be better appreciated. In FIG. 1, the pulse rate monitoring system 10 is mounted to the treadmill 12 while, in FIG. 3, the pulse rate monitoring system 10 is mounted to a stationary bicycle 68. Again, the pulse rate monitoring system 10 is mounted to a support frame 70 not particularly well suited for the mounting of electrodes thereto. For the treadmill 12, the preferred location for mounting the first and second tubular members 26 and 28 were the side bars 16 and 20 which were integrally formed with the remainder of the support frame 16. For the stationary bicycle 68, the preferred location for mounting the first and second tubular members 26 and 28 are near ends of handlebars 72 which are in very close proximity with each other. Thus, neither of the support frames 16 or 70 are configured to permit the tubular members 26 and 28 to be slid thereonto. Finally, it should now be appreciated that the pulse rate monitoring system 10 is suitable for use with a wide variety of types of exercise machines and may be readily removed from a first exercise machine and mounted onto another exercise machine.

Although an illustrative embodiment of the invention has been shown and described, other modifications, changes, and substitutions are intended in the foregoing disclosure. Accordingly, it is appropriate that the appended claims be construed broadly and in a manner consistent with the scope of the invention.

What is claimed is:

1. A removably mountable pulse rate monitoring system, comprising:

a tubular member having at least one electrode disposed on an outer side surface thereof, said tubular member having an interior space and first and second interior side surface which define an access opening for accessing said interior space, said access opening longitudinally extending along the length of said tubular member; and a pulse rate monitor electrically connected to said at least one electrode disposed on said tubular member;

wherein said first interior side surface is movable, relative to said second interior side surface, between a first position in which said first and second interior side surfaces engage each other and said access opening is closed and a second position in which said first and second interior side surfaces are spaced apart from each other and said access opening is open.

2. The pulse rate monitoring system of claim 1 wherein said tubular member has an inner side surface which defines said interior space.

3. A pulse rate monitoring system, comprising:

a tubular member having at least one electrode disposed on an outer side surface thereof, said tubular member being openable along its length; and a pulse rate monitor electrically connected to said at least one electrode disposed on said tubular member;

wherein said tubular member further comprises:

a first part having an outwardly curved top surface, an inwardly curved bottom surface and first and second side surfaces;

a second part having an outwardly curved top surface, an inwardly curved bottom surface and first and second side surfaces;

said first side surface of said first part pivotably mounted to said first side surface of said second part;

said first part pivotable, relative to said second part, from a first position in which said second side surface of said first part engages said second side surface of said second part and said first and second parts collectively form an open ended tube having a first length and an interior area defined by said bottom surfaces of said first and second parts to a second position in which said second side surface of said first part is spaced apart from said second side surface of said second part to define an access opening through which a bar having a second length greater than said first length may be inserted.

4. The pulse rate monitor of claim 3 wherein each one of said first and second parts further comprise at least one hinge tab, each one of said at least one hinge tab of said first part attached to a corresponding one of said at least one hinge tab of said second part to pivotably mount said first part to said second part.

5. The pulse rate monitoring system according to claim 4 and further comprising a biasing spring mounted between first and second ones of said at least one hinge tabs, said biasing spring biasing said second side surface of said first part into engagement with said second side of said first part.

6. The pulse rate monitor of claim 3 wherein said tubular member further comprises:

a first electrode mounted on said top surface of said first part; and a second electrode mounted on said top surface of said second part;

said first and second electrodes electrically connected to said pulse rate monitor.

7. For an exercise machine having a support bar system comprised of at least one support bar positioned for grasping by a user of said exercise machine while exercising, a pulse rate monitoring system, comprising:

a pulse rate calculation circuit;

a display, coupled to said pulse rate calculation circuit, for displaying a pulse rate determined by said pulse rate calculation circuit;

said pulse rate calculation circuit and said display supportably mounted by a first housing configured for removable attachment to said support bar system;

a first electrode coupled to said pulse rate calculation circuit;

a second electrode coupled to said pulse rate calculation circuit;

said first and second electrodes transmitting data used to determine said pulse rate of said user to said pulse rate calculation circuit when said first and second electrodes are grasped by said user;

said first electrode supportably mounted by a second housing configured for removable attachment to said support bar system; and said second electrode supportably mounted by a third housing configured for removable attachment to said support bar system.

8. The pulse rate monitoring system according to claim 7 wherein:

said second housing is a first, generally tubular, sidewall having an outer surface on which said first electrode is mounted, an inner surface which defines an interior space, a first side surface which extends along the length of said first sidewall and a second side surface which extends along the length of said first sidewall;

said second housing being deformable to space said first side surface apart from said second side surface to define an access aperture which extends along the length of said first sidewall;

said third housing is a second, generally tubular, sidewall having an outer surface on which said second electrode is mounted, an inner surface which defines an interior space, a first side surface which extends along the length of said second sidewall and a second side surface which extends along the length of said second sidewall;

said third housing being deformable to space said first side surface apart from said second side surface to define an access aperture which extends along the length of said second sidewall;

wherein said access aperture defined by said first and second side surfaces of said first sidewall enable said second housing to be placed over said support bar system at a first location and said access aperture defined by said first and second side surfaces of said second sidewall enable said third housing to be placed over said support bar system at a second location.

9. The pulse rate monitoring system of claim 8 wherein each one of said first and second tubular sidewalls have a first length, said support bar system includes a first support bar having a second length and wherein each one of said first and second tubular sidewalls further comprises:

a first part having an outwardly curved top surface, an inwardly curved bottom surface and first and second side surfaces;

a second part having an outwardly curved top surface, an inwardly curved bottom surface and first and second side surfaces;

said first side surface of said first part pivotably mounted to said first side surface of said second part;

said first part pivotable, relative to said second part, from a first position in which said second side surface of said first part engages said second side surface of said second part to a second position in which said second side surface of said first part is spaced apart from said second side surface of said second part to define an access opening through which said support bar may be inserted.

10. The pulse rate monitor of claim 9 wherein each one of said first and second parts further comprise at least one hinge tab, each one of said at least one hinge tab of said first part attached to a corresponding one of said at least one hinge tab of said second part to pivotably mount said first part to said second part.

11. The pulse rate monitoring system according to claim 10 and further comprising a biasing spring mounted between first and second ones of said at least one hinge tabs, said biasing spring biasing said second side surface of said first part into engagement with said second side of said first part.

12. The pulse rate monitoring system of claim 11 wherein:

said first housing has a first exterior side surface, a second exterior side surface, an interior side surface which defines an interior space in which said pulse rate calculation circuit is positioned and a interior passageway extending from said first exterior side surface, through said interior space, and to said second exterior side surface.

13. The pulse rate monitoring system of claim 12 and further comprising:

a first electrical cable having a first end coupled to said first electrode and a second end coupled to said pulse rate calculation circuit;

a second electrical cable having a first end coupled to said second electrode and a second end coupled to said pulse rate calculation circuit;

said first and second electrical cable accessing said pulse rate calculation circuit through said passageway.

14. The pulse rate monitoring system of claim 13 wherein said first housing is clamped over said support bar such that said support bar extends through said passageway.

15. An exercise machine, comprising:

a platform;

a support frame mounted to said platform; and a pulse rate monitoring system mounted to said support frame, said pulse rate monitoring system comprising:

a pulse rate calculation circuit;

a display, coupled to said pulse rate calculation circuit, for displaying a pulse rate determined by said pulse rate calculation circuit;

said pulse rate calculation circuit and said display supportably mounted by a first housing configured for removable attachment to said support frame;

a first electrode coupled to said pulse rate calculation circuit;

a second electrode coupled to said pulse rate calculation circuit;

said first and second electrodes transmitting data used to determine said pulse rate of said user to said pulse rate calculation circuit when said first and second electrodes are grasped by said user;

said first electrode supportably mounted by a second housing configured for removable attachment to said support frame; and said second electrode supportably mounted by a third housing configured for removable attachment to said support frame.

16. The exercise machine according to claim 15 wherein:

said second housing is a first, generally tubular, sidewall having an outer surface on which said first electrode is mounted, an inner surface which defines an interior space, a first side surface which extends along the length of said first sidewall and a second side surface which extends along the length of said first sidewall;

said second housing being deformable to space said first side surface apart from said second side surface to define an access aperture which extends along the length of said first sidewall;

said third housing is a second, generally tubular, sidewall having an outer surface on which said second electrode is mounted, an inner surface which defines an interior space, a first side surface which extends along the length of said second sidewall and a second side surface which extends along the length of said second sidewall;

said third housing being deformable to space said first side surface apart from said second side surface to define an access aperture which extends along the length of said second sidewall;

wherein said access aperture defined by said first and second side surfaces of said first sidewall enable said second housing to be placed over said support frame at a first location and said access aperture defined by said first and second side surfaces of said second sidewall enable said third housing to be placed over said support frame at a second location.

17. The exercise machine of claim 16 wherein each one of said first and second tubular sidewalls have a first length, said support frame has a second length and wherein each one of said first and second tubular sidewalls further comprises:

a first part having an outwardly curved top surface, an inwardly curved bottom surface and first and second side surfaces;

a second part having an outwardly curved top surface, an inwardly curved bottom surface and first and second side surfaces;

said first side surface of said first part pivotably mounted to said first side surface of said second part;

said first part pivotable, relative to said second part, from a first position in which said second side surface of said first part engages said second side surface of said second part to a second position in which said second side surface of said first part is spaced apart from said second side surface of said second part to define an access opening through which said support frame may be inserted.

18. A pulse rate monitoring system, comprising:

a first part having an outer side surface on which at least one electrode is disposed;

a second part;

a pulse rate monitor electrically connected to said at least one electrode disposed on said first part;

said first part pivotably mounted to said second part;

said first part pivotable, relative to said second part, from a first position in which said first and second parts collectively define a first open ended tube having a first length to a second position in which said first part is spaced apart from said second part to define a first access opening through which a bar having a second length, greater than said first length may be inserted.

19. The pulse rate monitoring system of claim 18 and further comprising:

a third part having an outer side surface on which at least one electrode is disposed; and a fourth part;

said third part pivotably mounted to said fourth part;

said third part pivotable, relative to said fourth part, from a third position in which said third and fourth parts collectively define a second open ended tube having a third length to a fourth position in which said third part is spaced apart from said fourth part to define a second access opening through which said bar may be inserted;

said second length being greater than said third length.

20. The pulse rate monitoring system of claim 19 and further comprising:

a housing configured for removable detachment to said bar;

said pulse rate monitor supportably mounted by said housing.

21. The pulse rate monitoring system of claim 20 wherein:

said second part has an outer side surface on which at least one electrode is disposed; and said fourth part has an outer side surface on which at least one electrode is disposed;

said pulse rate monitor electrically connected to said at least one electrode disposed on said second part and said at least one electrode disposed on said fourth part.

22. A method for installing a pulse rate monitoring system onto an exercise machine having a support bar system, comprising the steps of:

providing a first generally tubular insulative housing, said housing having an exterior side surface, an interior side surface which defines a generally cylindrical interior passageway and a normally closed access aperture which extends between said exterior side surface and said interior side surface;

mounting a first electrode onto said exterior side surface of said first housing;

attaching said first housing to said support bar system such that a first length of said support bar system is received within said generally cylindrical interior passageway by opening said access aperture, passing said first length of said support bar system through said access aperture and closing said access aperture.

23. The method of claim 22 and further comprising the steps of:

providing a second generally tubular insulative housing, said housing having an exterior side surface, an interior side surface which defines a generally cylindrical interior passageway and a normally closed access aperture which extends between said exterior side surface and said interior side surface;

mounting a second electrode onto said exterior side surface of said second housing; and attaching said second housing to said support bar system such that a second length of said support bar system is received within said generally cylindrical interior passageway by opening said access aperture, passing said second length of said support bar system through said access aperture and closing said access aperture.

24. The method of claim 23 and further comprising the step of:

attaching a pulse rate monitor onto said exercise machine, said pulse rate monitor electrically connected to said first and second electrodes;

said pulse rate monitor determining a pulse rate from data received from said first and second electrodes.

25. The method of claim 23 wherein said support bar system has a first side bar and a second side bar and wherein said first housing is clamped onto said first side bar and said second housing is clamped onto said second side bar.

26. The method of claim 23 wherein said support bar system has a front bar and said first and second housings are clamped onto said front bar.

* * * * *